United States Patent
Zeng et al.

(10) Patent No.: US 9,575,036 B2
(45) Date of Patent: Feb. 21, 2017

(54) METHOD FOR MEASURING ENCAPSULATION EFFICIENCY FOR HYDROPHOBIC ACTIVES

(71) Applicant: ROHM AND HAAS COMPANY, Philadelphia, PA (US)

(72) Inventors: Fanwen Zeng, Belle Mead, NJ (US); Boris Polanuyer, Lansdale, PA (US)

(73) Assignee: Rohm and Haas Company, Philadelphia, PA (US)

( * ) Notice: Subject to any disclaimer, the term of this patent is extended or adjusted under 35 U.S.C. 154(b) by 105 days.

(21) Appl. No.: 14/429,662

(22) PCT Filed: Sep. 18, 2013

(86) PCT No.: PCT/US2013/060277
§ 371 (c)(1),
(2) Date: Mar. 19, 2015

(87) PCT Pub. No.: WO2014/047101
PCT Pub. Date: Mar. 27, 2014

(65) Prior Publication Data
US 2015/0233871 A1 Aug. 20, 2015

Related U.S. Application Data

(60) Provisional application No. 61/704,664, filed on Sep. 24, 2012.

(51) Int. Cl.
*G01N 30/02* (2006.01)
*G01N 1/18* (2006.01)
*A61K 8/11* (2006.01)

(52) U.S. Cl.
CPC ............... *G01N 30/02* (2013.01); *A61K 8/11* (2013.01); *G01N 2030/027* (2013.01); *Y10T 436/143333* (2015.01); *Y10T 436/25375* (2015.01)

(58) Field of Classification Search
CPC ............ G01N 30/02; G01N 2030/027; A61K 2800/20; A61K 2800/40; A61K 8/11; A61Q 17/00; A61Q 17/04; Y10T 436/143333; Y10T 436/25; Y10T 436/25375
USPC ... 436/94, 161, 174, 177; 424/401; 73/61.52
See application file for complete search history.

(56) References Cited

U.S. PATENT DOCUMENTS

| 5,521,266 A | 5/1996 | Lau | |
| 2009/0232881 A1* | 9/2009 | Bandyopadhyay | A61K 8/14 424/450 |
| 2011/0104283 A1* | 5/2011 | Mousa | A61K 9/5146 424/487 |
| 2014/0271752 A1* | 9/2014 | Zeng | A61Q 17/04 424/401 |

FOREIGN PATENT DOCUMENTS

WO 2006/133518 A1 12/2006

OTHER PUBLICATIONS

Jia Le-jiao et al.,; Chin Pharm J, Sep. 2009, vol. 44, No. 18, pp. 1400-1403.
Shen,Gao; New Dose Forms and Technologies in Modern Pharmacy; People's Military Medical Publisher; Jan. 2002, pp. 103-105.
Yang, J. et al: "Influence of Hydroxypropyl-Beta-Cyclodextrin on Transdermal Penetration and Photostability of Avobenzone", European Journal of Pharmaceutics and Biopharmaceutics, Elsevier Science Publishers B.V., Amsterdam, NL, vol. 69, No. 2, Jun. 1, 2008, pp. 605-612, XP922664276.

* cited by examiner

*Primary Examiner* — Maureen Wallenhorst
(74) *Attorney, Agent, or Firm* — Edward L. Brant

(57) ABSTRACT

Described are methods of determining free hydrophobic active in aqueous formulations including the steps of encapsulating a hydrophobic active, preparing a formulation containing encapsulated hydrophobic active, adding a cyclodextrin to the formulation, thereby entraining any free hydrophobic active; and quantifying the amount of free hydrophobic active.

6 Claims, No Drawings

METHOD FOR MEASURING ENCAPSULATION EFFICIENCY FOR HYDROPHOBIC ACTIVES

CROSS-REFERENCE TO RELATED APPLICATION(S)

This application claims priority to and is a 371 U.S.C. §371 national phase application of International Application No. PCT/US/2013/060277, filed on Sep. 18, 2013, which claims the priority benefit of U.S. Provisional Application No. 61/704,664, filed on Sep. 24, 2012, each of which is incorporated herein by reference.

BACKGROUND

Encapsulation of hydrophobic actives is an incredibly important area of research, affecting the personal care, home care, antimicrobial, life science, and agricultural industries. Generally, encapsulation is on the micro scale, and protects the hydrophobic active from decomposition or unwanted interactions with other materials in the formulation, as well as sometimes providing controlled release.

There are a number of conventional encapsulation technologies, such as aqueous polyurethane dispersions, polyurea dispersion, melamine-formaldehyde dispersions, poly (meth)acrylate dispersions, and urea-formaldehyde dispersions, and it is important that the encapsulation efficiency be tested in order to determine where improvement can occur. However, depending on shell thickness and cross-linking chemistry and density, some encapsulated particles are too fragile to be tested by conventional organic solvent extraction methods. It should be understood that testing such particles by conventional methods leads to rupture or release of the hydrophobic active, and hence inaccurate determination of un-encapsulated (or free) hydrophobic active.

Therefore, what is needed are new test methods that are less disruptive.

DETAILED DESCRIPTION

In one embodiment, the present invention includes methods of determining free hydrophobic active in aqueous formulations, comprising, encapsulating a hydrophobic active, preparing a formulation comprising encapsulated hydrophobic active, adding a cyclodextrin to the formulation, thereby entraining any free hydrophobic active; and quantifying the amount of free hydrophobic active.

"Hydrophobic active" refers to a non-water soluble ingredient that is recognized in the art as a beneficial agent, i.e., one conferring a direct performance benefit in personal care, home care, antimicrobial, life science, or agricultural use. By way of a non-limiting example, avobenzone is a hydrophobic active ingredient for a sunscreen formulation, whereas white petrolatum is not, although it is useful as an emollient.

"Aqueous formulation" refers to water-based formulations. In one embodiment, the aqueous formulation is a water-based emulsion or a water-based microemulsion. Non-limiting examples of aqueous formulations of the present inventions include sunscreens, aqueous fragrance formulations, antimicrobial control formulations, pesticide, insecticide formulations, fabric softeners, detergents, personal care and hygiene products, anti-fouling formulations, and herbicides.

In one embodiment, the hydrophobic active is encapsulated via conventional encapsulation technologies, such as aqueous polyurethane dispersions, polyurea dispersion, melamine-formaldehyde dispersions, poly(meth)acrylate dispersions, and urea-formaldehyde dispersions. Non-limiting examples of methods of encapsulating actives include those described in patent publications US 2010/0260687, US 2011/0059144, US 2010/0310671, WO98/03065, among others. In one embodiment, the hydrophobic active is encapsulated via new developmental encapsulation technologies.

In operation, the presently described methods find use because no encapsulation technology is one hundred percent efficient, and it is necessary to quantify how much hydrophobic active remains un-encapsulated, this un-encapsulated portion being referred to herein as "free hydrophobic active."

Cyclodextrins are cyclic polysaccharides with a large hydrophobic cavity. In one embodiment, the cyclodextrin is alpha-cyclodextrin (see structure I, below). In one embodiment, the cyclodextrin is beta-cyclodextrin (see structure II, below).

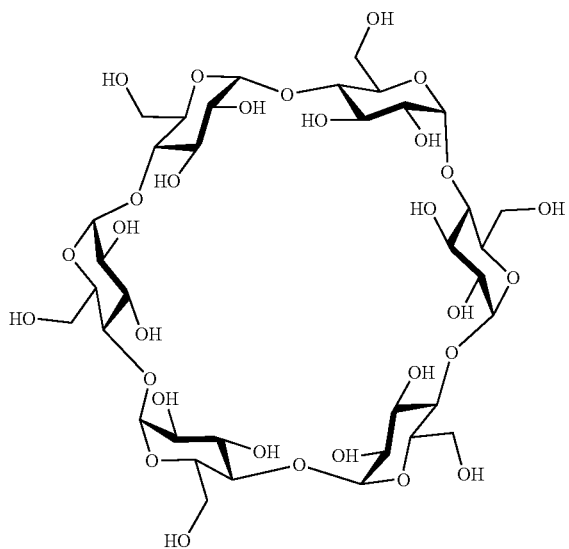

I

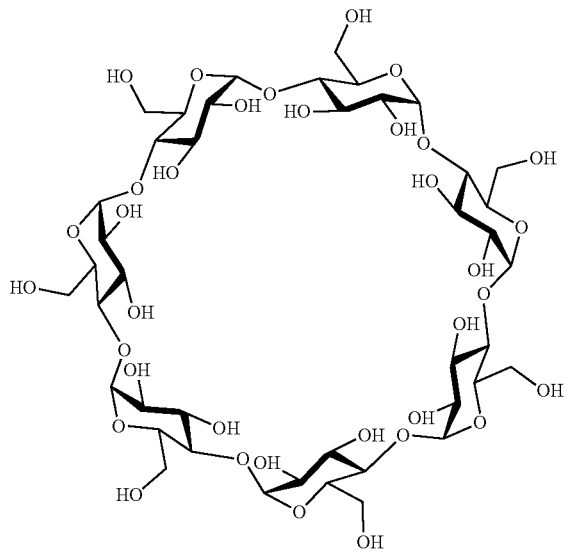

II

In one embodiment, the cyclodextrin is a mixture of alpha-cyclodextrin and beta-cyclodextrin. In one embodiment, the cyclodextrin is a gamma-cyclodextrin. In one embodiment, the cyclodextrin is a methyl, triacetyl hydroxypropyl or hydroxyethyl derivative of cyclodextrin derivative.

In one alternative embodiment, the cyclodextrin is combined with a cyclic oligosaccharide having a hydrophobic cavity, such as cycloinulohexose, cycloinuloheptose, cycloinuloctose, calyxarenes, and or cavitands. In one alternative embodiment, the cyclodextrin is replaced by at least one of cycloinulohexose, cycloinuloheptose, cycloinuloctose, calyxarenes, and or cavitands.

Without being bound by theory, it is believed that in aqueous environments, any un-encapsulated hydrophobic active becomes complexed with the hydrophobic interior of the cyclodextrins. Regardless of theory, we have observed a very high binding constant in water between the hydrophobic actives and the cyclodextrins. Accordingly, it is an essential feature that the method be used with aqueous formulations.

In one embodiment, the cyclodextrin is added as a solid. However, in a preferred embodiment, the cyclodextrin is added as an aqueous solution. In one embodiment, the cyclodextrin solution is 25% solids. In one embodiment, the cyclodextrin is added as an aqueous solution and diluted to 25% solids with respect to the formulation containing microencapsulated components.

In one embodiment, after adding a cyclodextrin to the formulation containing microencapsulated components, an additional step of centrifuging the formulation is performed. The fraction containing the cyclodextrin and complexed hydrophobic active is removed. The obtained complex can be analyzed using conventional HPLC methods for detecting the desired hydrophobic active.

One advantage of the present invention is that the un-encapsulated hydrophobic active is extracted under relatively gentle conditions, without using organic solvents, for example, xylene, toluene, benzene, and the like.

EXAMPLES

The following examples are illustrative of some embodiments of the present invention.

Example 1

To test the methods of the present invention, a formulation containing a microencapsulated sunscreen active ("Batch A") is prepared by making an aqueous phase by first dissolving polyvinyl alcohol (PVA; CELVOL 205 from Celanese) in water with heating to 90° C. to form a PVA solution. The PVA solution is cooled to 55° C. An oil phase is prepared by first mixing UV absorbers, 1 part Homosalate (3,3,5-Trimethylcyclohexyl 2-hydroxybenzoate (PARSOL®)), 1 part octocrylene (2-ethylhexyl 2-cyano-3,3-diphenyl-2-propenoate (PARSOL® 340)) and 2 parts Avobenzone (Butyl methoxydibenzoylmethane (PARSOL® 1789)) with heating to 80° C. 7 g of polymethylene polyphenylisocyanate (PAPI™ 27) is added to 93 g of the mixture of UV absorbers at 55° C. with gentle mixing to form the oil phase. The aqueous phase is transferred to the oil phase slowly while both are maintained at a temperature of 50° C. The mixture is subjected to shear with a Silverson high shear homogenizer at a shear rate of 9000 rpm for 5 to 10 minutes. Then the emulsion is treated with a solution of 4.6 g of ethylenediamine in 41.8 g of water and mixed for 20 minutes at 50° C. to form the microencapsulated avobenzone slurry (11.92% Avo.).

Example 2 (Comparative)

To conventionally determine the efficiency of the encapsulation method of Example 1, i.e., to quantify the amount of un-encapsulated Avobenzone in Batch A, a formulation substantially according to Example 1 is prepared.

Using a conventional solvent (Xylene) extraction process, into a vial is added 100-200 mg of Batch A followed by 5 mL of DI water. The diluted slurry is mixed for 30 min with an orbital shaker. Then, 5 mL of xylene is added to the slurry followed by mixing for the time listed in Table 1.

The organic (top) layer is separated through centrifugation at 16,000 rpm for 15 minutes. The clear supernatant is siphoned with a pipette and used for HPLC analysis. The conditions for HPLC analysis are described as below:

Column: Restek Ultra C18 150×4 mm (or equivalent).
Mobile phase: Acetonitrile: water (V/V): 73:27
Flow rate: 2.5 mL/min
Run time: 8 min isocratic
Detection: 310 nm (homosalate/oxocrylene/avobenzone) or 360 nm (avobenzone only).

Table 1 shows the percentage of un-encapsulted Avobenzone detected over time (calculated as the ratio of detected Avobenzone level vs. the total theoretical Avobenzone level).

TABLE 1

| Time (hour) | Percentage of un-encapsulated Avobenzone detected (Comparative) |
| --- | --- |
| 0.5 | 5.8 |
| 1 | 20.6 |
| 2 | 25.9 |
| 3 | 34.5 |
| 4 | 39.2 |
| 6 | 43.6 |
| 24 | 83.4 |

Accordingly, the conventional solvent extraction appears to have a serious problem quantifying un-encapsulated Avobenzone (which should not be increasing over time). Without wishing to be bound by theory, it appears that the organic solvent initially under-detects the free active, and then leaches or undesirably extracts the Avobenzone from the microcapsules over time.

Example 3

To determine the efficiency of the encapsulation method of Example 1, i.e., to quantify the amount of un-encapsulated Avobenzone in Batch A, according to one embodiment of the present invention, a formulation substantially according to Example 1 is prepared.

Measurement of un-encapsulated Avobenzone through complexation with cyclodextrin is accomplished as follows. Into a vial is added 100-200 mg of Batch A followed by 5 mL of DI water and 5 mL of cyclodextrin solution (50% by weight, Cavasol W7M TL, supplied by Wacker Chemical) in water. The diluted slurry is mixed for 1, 2, 3, and 4 hours respectively with an orbital shaker. 1 mL of mixture is removed and centrifuged at 16,000 rpm for 15 minutes. The clear supernatant is siphoned with a pipette and used for HPLC analysis. The conditions for HPLC analysis are described as above (Column: Restek Ultra C18 150×4 mm (or equivalent); Mobile phase: Acetonitrile: water (V/V): 73:27; Flow rate: 2.5 mL/min; Run time: 8 min isocratic; Detection: 310 nm (homosalate/oxocrylene/avobenzone) or 360 nm (avobenzone only)).

Table 2 shows the percentage of un-encapsulted Avobenzone detected over time (calculated as the ratio of detected Avobenzone level vs. the total theoretical Avobenzone level).

TABLE 2

| Time (hour) | Percentage of un-encapsulated Avobenzone detected |
|---|---|
| 1 | 22.7 |
| 2 | 25.0 |
| 3 | 22.0 |
| 4 | 24.3 |

As can be seen, this embodiment of the present invention provides a method of quantifying un-encapsulated Avobenzone that is reasonably steady over time.

The invention claimed is:

1. A method of determining free hydrophobic active in an aqueous formulation, comprising:
    encapsulating a hydrophobic active in the aqueous formulation, wherein the encapsulating comprises the formation of an aqueous dispersion selected from the group consisting of polyurethane dispersions, polyurea dispersions, melamine-formaldehyde dispersions, and urea-formaldehyde dispersions;
    adding a cyclodextrin to the aqueous formulation, thereby entraining any free hydrophobic active;
    centrifuging the aqueous formulation to obtain a fraction containing cyclodextrin and entrained hydrophobic active;
    removing the fraction containing cyclodextrin and entrained hydrophobic active; and
    quantifying the amount of hydrophobic active entrained in the cyclodextrin.

2. The method of claim 1, wherein the cyclodextrin is alpha-cyclodextrin.

3. The method of claim 1, wherein the cyclodextrin is beta-cyclodextrin.

4. The method of claim 1, further comprising adding at least one cyclodextrin derivative, cycloinulohexose, cycloinuloheptose, cycloinuloctose, calyxarenes, or cavitands to the formulation.

5. The method of claim 1, wherein the step of quantifying the amount of hydrophobic active entrained in the cyclodextrin is performed using HPLC.

6. The method of claim 1, wherein the hydrophobic active is a personal care active.

* * * * *